US00PP32213P2

(12) United States Plant Patent
O'Connell

(10) Patent No.: US PP32,213 P2
(45) Date of Patent: Sep. 15, 2020

(54) ***PORTULACARIA* PLANT NAMED 'MANNY'**

(50) Latin Name: *Portulacaria afra*
Varietal Denomination: MANNY

(71) Applicant: Altman Specialty Plants, Inc, Vista, CA (US)

(72) Inventor: Renee O'Connell, Escondido, CA (US)

(73) Assignee: Atman Specialty Plants, Inc, Vista, CA (US)

( * ) Notice: Subject to any disclaimer, the term of this patent is extended or adjusted under 35 U.S.C. 154(b) by 0 days.

(21) Appl. No.: 16/501,790

(22) Filed: Jun. 6, 2019

(51) Int. Cl.
*A01H 5/00* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Portulacaria* cultivar named 'MANNY' is disclosed, characterized by plants that produce upright branches with rounded leaves. Foliage is distinctively thickened and has consistent unique marginal and marbled variegation. The new variety is a *Portulacaria*, typically produced as a garden or container plant.

3 Drawing Sheets

Latin name of the genus and species: *Portulacaria afra*. Variety denomination: 'MANNY'.

BACKGROUND OF THE INVENTION

The new cultivar is a product of a naturally occurring mutation in a commercial nursery in Vista, Calif. The parent is *Portulacaria afra* 'Variegate', unpatented. 'MANNY' was found and selected by the inventor in Vista, Calif. in April 2014.

Asexual reproduction of the new cultivar 'MANNY' was first performed by vegetative cuttings at a commercial greenhouse in Vista, Calif. in June 2014. 'MANNY' has since produced at least 15 generations and has shown that the unique features of this cultivar are stable and reproduced true to type.

SUMMARY OF THE INVENTION

The cultivar 'MANNY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MANNY'. These characteristics in combination distinguish 'MANNY' as a new and distinct *Portulacaria* cultivar:

1. Produces upright branches of rounded leaves, with some leaf margins randomly crenulate.
2. Produces thickened leaves.
3. Displays a unique marginal and marbled variegation.

PARENTAL COMPARISON

Plants of the new cultivar 'MANNY' are similar to the seed parent in most horticultural characteristics. However, plants of the new variety differ from the seed parent in the following:

1. *Portulacaria afra* 'Manny' exhibits wider, orbicular to broad spatulate leaves, as compared with the narrower ovoid shaped leaves of *Portulacaria afra* 'Variegata'.
2. *Portulacaria afra* 'Manny' displays an unusual subtle variegation, producing an overall marbled mint green colored leaf, with slender pale yellow margins, in contrast to the more distinctly marked variegation of *Portulacaria afra* 'Variegata', which produces leaves that are mint green in the center, with wide margins of pale yellow.
3. *Portulacaria afra* 'Manny' produces thickened leaves, as compared to the thinner leaves of *Portulacaria afra* 'Variegata'.
4. *Portulacaria afra* 'Manny', due to the rounder leaves, creates a fuller appearing commercial product using less cuttings, in contrast to *Portulacaria afra* 'Variegata', which requires more cuttings to give the same appearance of a full plant.

COMMERCIAL COMPARISON

'Manny' can be compared to the unpatented commercial variety *Portulacaria afra* 'Variegata Prostrata'. The two *Portulacaria* varieties are similar in most horticultural characteristics; however, the new variety differs in the following:

1. *Portulacaria afra* 'Manny' exhibits wider, orbicular to broad spatulate leaves whereas *Portulacaria afra* 'Variegata Prostrata' has more ovoid leaves.
2. *Portulacaria afra* 'Manny ' has leaves that are more thickened, whereas *Portulacaria afra* 'Variegata Prostrata' has thinner leaves.
3. *Portulacaria afra* 'Manny ' displays leaves that are have marbled variegation throughout, as well as marginal variegation, whereas the leaves of *Portulacaria afra* 'Variegata Prostrata' are solid green medially, with equal wide margins of pale yellow.

4. *Portulacaria afra* 'Manny ' grows with an upright morphology; whereas *Portulacaria afra* 'Variegata Prostrata' grows with a pendulous habit.

'Manny' can also be compared to an unnamed, unpatented variety *Portulacaria afra*. The two *Portulacaria* varieties are similar in most horticultural characteristics; however, the new variety differs in the following:

1. *Portulacaria afra* 'Manny' is a variegate, whereas *Portulacaria afra* is monotone emerald green in color.
2. *Portulacaria afra* 'Manny' produces thickened leaves, whereas those of *Portulacaria afra* are not thickened.
3. *Portulacaria afra* 'Manny' exhibits rounded leaves, in contrast to the ovoid leaves of *Portulacaria afra*.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Portulacaria afra* 'Manny'. Photographs provided by the breeder.

DETAILED BOTANICAL DESCRIPTION

Figure 1:
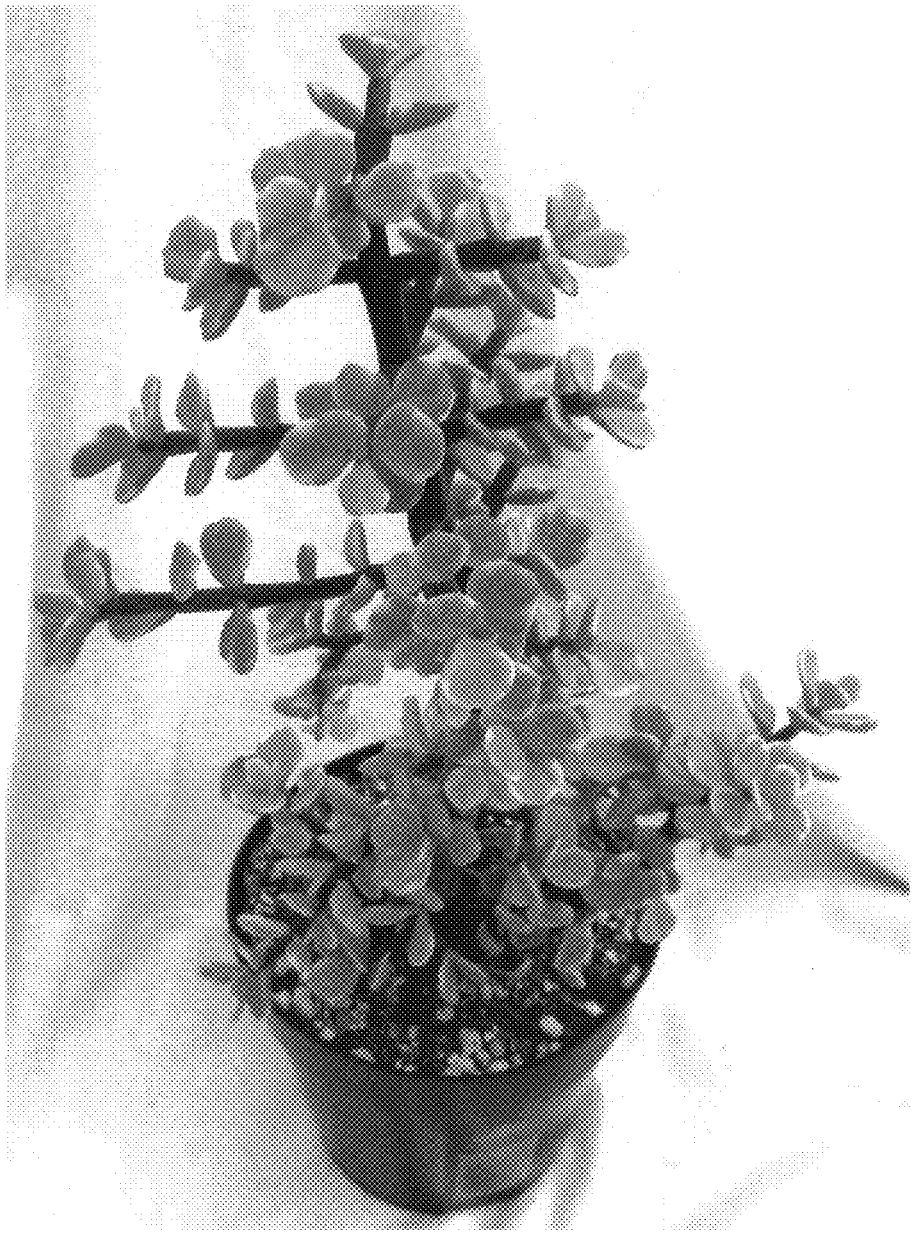
FIG. 1 illustrates in full color the plant of *Portulacaria afra* 'Manny' described, grown in a greenhouse (approximately 2500 foot candles) in Vista, Calif. The plant is approximately 4 to 5 months old.
Figure 2:
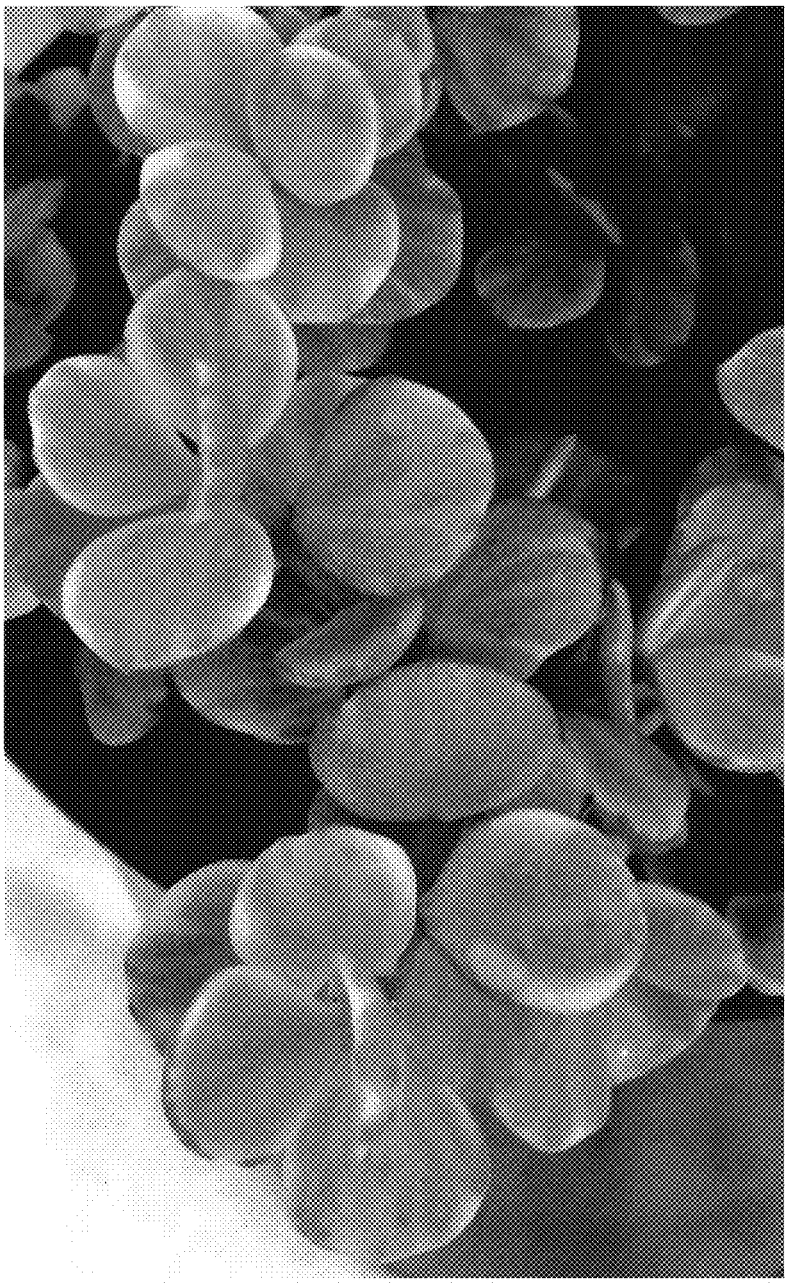
FIG. 2 illustrates in full color a closeup of the *Portulacaria afra* 'Manny' described, grown in a greenhouse (approximately 2500 foot candles) in Vista, Calif. The plant is approximately 4 to 5 months old.
Figure 3:
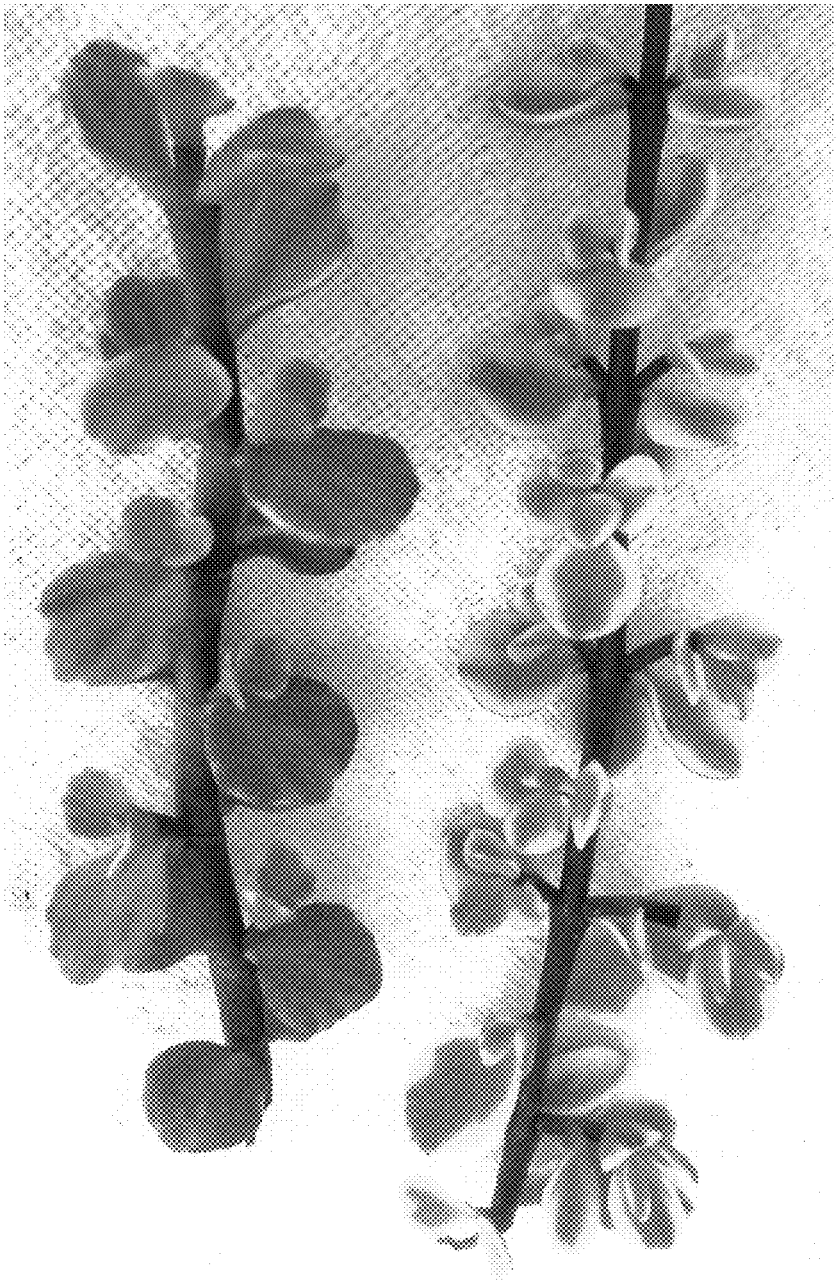
FIG. 3 illustrates in full color a closeup of a branch of *Portulacaria afra* 'Manny', (on the left of the photo), as compared to a branch of *Portulacaria afra* 'Variegata', (on the right) both grown in a greenhouse (approximately 2500 foot candles) in Vista, Calif. The plant is approximately 4 to 5 months old.

In the following description, color references are made to The Royal Horticultural Society Color Chart, 2007 edition, except where general terms of ordinary dictionary significance are used. The following observations and measurements describe 'MANNY' plants in a commercial shadehouse in Vista, Calif. Temperatures ranged from 34° F. to 90° F. during the night and day. No artificial light, photoperiodic treatments or chemical treatments were given to the plants. Natural light conditions were approximately 3000 to 4000 foot candles of light. Measurements and numerical values represent averages of typical plant types.

Botanical classification: *Portulacaria afra* 'MANNY'.

PROPAGATION

Time to initiate roots: Approximately 25 days at 22° C.
Root description: Densely fibrous.
Propagation method: Vegetative cuttings.
Root color: Near RHS Brown 200D.

PLANT

Age of the plant described: Approximately 4 to 5 months.
Growth habit: Upright, with lateral branches occurring at angles of 15 to 85° from center. Acute angles most common.
Container size: 5 inches.
Height: Approximately 32 cm.
Plant spread: Approximately 18 cm, in a 5 inch pot.
Growth rate: Rapid.
Branching characteristics: Opposite. Each opposite pair occurring 90° from above pair. Little or no sub-lateral branches at this stage of maturity.
Length of lateral branches: Average range 3 to 8 cm.
Diameter of lateral branches: Approximately 3 to 5 mm.
Quantity branches: 20 to 24 large main lateral branches, from each main stem.
*Texture*.—Glabrous.
*Shape*.—Round.
*Color*.—Near RHS Greyed-Purple 187C.

FOLIAGE

Leaf:
*Arrangement*.—Opposite.
*Average length*.—Average range 1.2 to 1.9 cm.
*Average width*.—Average range 1.2 to 1.7 cm.
*Average depth*.—3 to 4 mm.
*Shape of blade*.—Broad spatulate to orbicular.
*Apex*.—Broad rounded, mucronate.
*Base*.—Broad taper.
*Margin*.—Entire.
*Texture of top surface*.—Glabrous.
*Texture of bottom surface*.—Glabrous.
*Appearance of top surface*.—Moderately glossy.
*Appearance of lower surface*.—Slightly glossy.
*Quantity of leaves per branch*.—Approximately 200.
*Color*.—Young foliage upper side: RHS Green 139C marginal streaks near Yellow 8D, interior blade streaks near Yellow-Green 145D. Young foliage, under side: RHS Green N138D, interior blade steaked 137C, marginal streaks near Yellow 8D. Mature foliage upper side: RHS Green N138D, marginal streaks near Yellow 8D, interior blade streaks near Yellow-Green 145D. Mature foliage, under side: RHS Green N138D, marginal and central streaks near Green 139D.
*Venation*.—There is no visual appearance of venation.
*Attachment*.—Sessile.

FLOWER

Flowering not observed.

OTHER CHARACTERISTICS

Fruits and seeds: Not observed to date.
Temperature tolerance: USDA zones 10 and above.
Disease/pest resistance: Neither resistance nor susceptibility to standard pathogens or pests of *Portulacaria* observed.
Drought tolerance: Extreme tolerance for drought.

What is claimed is:

1. A new and distinct cultivar of *Portulacaria* plant named 'MANNY' as herein illustrated and described.

* * * * *